United States Patent [19]
Wallace et al.

[11] Patent Number: 6,024,765
[45] Date of Patent: *Feb. 15, 2000

[54] VASO-OCCLUSIVE COIL WITH CONICAL END

[75] Inventors: Michael P. Wallace, Pleasanton; Francisco S. Villar, Newark; Nga Thi Van, Santa Clara; Nestor Aganon, Fremont; Delilah Hui, Daly City, all of Calif.

[73] Assignee: Target Therapeutics, Inc., Fremont, Calif.

[*] Notice: This patent is subject to a terminal disclaimer.

[21] Appl. No.: 09/038,468

[22] Filed: Mar. 11, 1998

Related U.S. Application Data

[63] Continuation of application No. 08/774,504, Dec. 30, 1996, Pat. No. 5,733,329.

[51] Int. Cl.⁷ ....................................................... A61F 2/06
[52] U.S. Cl. ..................................................................... 623/1
[58] Field of Search .................................... 623/1, 11, 12; 606/151, 157, 153, 108, 191, 194, 195, 198

[56] References Cited

U.S. PATENT DOCUMENTS

| | | |
|---|---|---|
| 3,174,851 | 3/1965 | Buehler et al. . |
| 3,351,463 | 11/1967 | Rozner et al. . |
| 3,753,700 | 8/1973 | Harrison et al. . |
| 4,994,069 | 2/1991 | Ritchart et al. . |
| 5,098,374 | 3/1992 | Othel-Jacobsen et al. ............... 623/12 |
| 5,108,407 | 4/1992 | Geremia et al. . |
| 5,122,136 | 6/1992 | Guglielmi et al. . |
| 5,234,437 | 8/1993 | Sepetka et al. . |
| 5,250,071 | 10/1993 | Palermo . |
| 5,261,916 | 11/1993 | Engelson . |
| 5,304,194 | 4/1994 | Chee et al. . |
| 5,304,195 | 4/1994 | Twyford, Jr. et al. . |
| 5,312,415 | 5/1994 | Palermo . |
| 5,334,210 | 8/1994 | Gianturco . |
| 5,350,397 | 9/1994 | Palermo et al. . |
| 5,354,295 | 10/1994 | Guglielmi et al. . |
| 5,382,259 | 1/1995 | Phelps et al. . |
| 5,413,586 | 5/1995 | Dibie et al. . |
| 5,514,176 | 5/1996 | Bosley, Jr. . |
| 5,522,836 | 6/1996 | Palermo . |
| 5,536,274 | 7/1996 | Neuss . |
| 5,556,413 | 9/1996 | Lam . |
| 5,578,074 | 11/1996 | Mirigian ....................................... 623/1 |
| 5,649,949 | 7/1997 | Wallace et al. ............................ 623/11 |
| 5,669,931 | 9/1997 | Kupiecki et al. ......................... 606/191 |
| 5,766,160 | 6/1998 | Samson et al. .......................... 606/108 |

FOREIGN PATENT DOCUMENTS

| | | |
|---|---|---|
| 0734697 | 10/1996 | European Pat. Off. . |
| 0747012 | 12/1996 | European Pat. Off. . |
| 0795300 | 9/1997 | European Pat. Off. . |
| 3203410 | 11/1982 | Germany . |
| WO 95/25480 | 9/1995 | WIPO . |

*Primary Examiner*—Todd E. Manahan
*Assistant Examiner*—Eduardo C. Robert
*Attorney, Agent, or Firm*—Morrison & Foerster, LLP

[57] ABSTRACT

This is an implantable vaso-occlusive coil which is implanted using minimally invasive surgical techniques. It is a complex, helically wound coil made up of a primary helically wound coil which is then wound into a specific secondary shape. The secondary shape is itself a series of helical turns. At least a portion of the turns in the secondary shape form a cylindrical region and adjacent that region on at least one end is a conical region which tapers from a diameter approximating that of the central cylindrical region to a smaller diameter. The device is desirably self-forming upon exit from the distal end of a delivery catheter. Also, the conical tipped vaso-occlusive device may also utilize thrombus-enhancing filamentary material.

19 Claims, 3 Drawing Sheets

VASO-OCCLUSIVE COIL WITH CONICAL END

CROSS-REFERENCE TO RELATED APPLICATIONS

This application is a continuation application of U.S. application Ser. No. 08/774,504 filed Dec. 30, 1996, now U.S. Pat. No. 5,733,329.

FIELD OF THE INVENTION

This invention is an implantable vaso-occlusive coil which is implanted using minimally invasive surgical techniques. It is a complex, helically wound coil made up of a primary helically wound coil which is then wound into a specific secondary shape. The secondary shape is itself a series of helical turns. At least a portion of the turns in the secondary shape fonn a cylindrical region and adjacent that region on at least one end is a conical region which tapers from a diameter approximating that of the central cylindrical region to a smaller diameter. The device is desirably self-forming upon exit from the distal end of a delivery catheter. Also, the conical tipped vaso-occlusive device may also utilize thrombus-enhancing filamentary material.

BACKGROUND OF THE INVENTION

Vaso-occlusive devices are surgical implements or implants that are placed within some opening in the human body. Typically the opening is either within the vasculature or some other region which is to be occluded. Such other sites include fallopian tubes and bile ducts. They are delivered typically via a catheter. It is intended that the devices either block the flow of blood through a vessel making up that portion of the vasculature via the formation of an embolus. An embolus may also be formed within an aneurysm stemming from a normal vessel by use of this invention.

One such widely used device is the helically wound vaso-occlusive coil. Many such coils are dimensioned to engage the walls of the vessels or other sites they are intended to occlude. Other significantly less stif helically wound devices have also been described in the literature.

A patent describing an early vaso-occlusive device which patent, parenthetically, also provides an excellent background to the vaso-occlusive technology at that time is Ritchart et al. (U.S. Pat. No. 4,994,069). Ritchart et al. describes a vaso-occlusive coil that assumes a linear helical configuration when stretched and a folded, convoluted configuration when released from the catheter. The stretched condition is used in placing the coil at the desired site via passage through the catheter. The coil assumes a relaxed configuration—which is better suited to occlude the vessel—once the device is released from the catheter. Ritchart et al describes a variety of secondary shapes including "flower" shapes and double vortices.

The use of vaso-occlusive coils having attached fibrous elements in a variety of secondary shapes is shown in Chee et al. (U.S. Pat. No. 5, 304,194). Chee et al. describes a helically wound device having a secondary shape in which the fibrous elements extend in a sinusoidal fashion down the length of the coil. These coils, as with the Ritchart et al. coils, are produced in such a way that they will pass through the lumen of a catheter in a generally straight configuration and, when released from the catheter, form a relaxed or secondary shape in the lumen or cavity chosen within the human body. The fibrous elements shown in Chee et al. enhance the ability of the coil to fill space within the vasculature and to facilitate formation of an embolus and subsequent allied tissue.

There are a variety of ways of placing shaped and linear coils into the human vasculature. In addition to those patents which are believed to describe only the physical pushing of a coil out into the vasculature, (e.g., Ritchart et al.), there are a number of other ways to release a coil at a specifically chosen time and site. For instance, U.S. Pat. Nos. 5,354,295 and its parent 5,122,136, both to Guglielmi et al. describe a device which is electrolytically detachable from its pusher wire.

A variety of mechanically detachable devices is also known. For instance, U.S. Pat. No. 5,234,437, to Sepetka, shows a coil which is helically unwound from a pusher having an interlocking surface. U.S. Pat. No. 5,250,071, to Palermo, shows an embolic coil assembly using interlocking clasps mounted both on the pusher and on the embolic coil. U.S. Pat. No. 5,261,916, to Engelson, shows a detachable pusher-vaso-occlusive coil assembly having an interlock ball and keyway-type coupling. U.S. Pat. No. 5,304,195, to Twyford et al., shows a pusher-vaso-occlusive coil assembly having an affixed, proximally extending wire carrying a ball on its proximal end and a pusher having a similar end. The two ends are interlocked and disengage when the coil is ejected from the distal end of the catheter. U.S. Pat. No. 5,312,415, to Palermo, shows a multiple coil device in which the coils are placed on a single pusher in the form of a guidewire which has a section capable of interconnecting with the interior of the helically wound coil. U.S. Pat. No. 5,350,397, to Palermo et al., shows a pusher having a throat at its distal end and a pusher through its axis. The pusher sheath will hold onto the end of an embolic coil and the embolic coil will then be released upon pushing of the axially placed pusher wire against the proximal portion of the vaso-occlusive coil.

Vaso-occlusive coils having little or no inherent secondary shape have also been described. For instance, in U.S. patent application Ser. No. 07/978,320, filed on Nov. 18, 1992, entitled "Ultrasoft Embolism Coils With Fluid-Like Properties" by Berenstein et al. is coil having little or no shape after introduction into the vascular space.

A variety of other patent applications assigned to Target Therapeutics, Inc., of Fremont, Calif. describe coils or other related vaso-occlusive devices having specific shapes. Of particular interest is U.S. design patent application Ser. No. 29/037,001 filed Mar. 31, 1995 for spiral vaso-occlusive coils by Mariant et al.

None of these previously-described devices or self-forming helically wound coils which self-form into secondary structures having opposing conical end separated by a generally cylindrical portion between those opposing ends.

SUMMARY OF THE INVENTION

This invention is a vaso-occlusive device comprising a helically wound coil which is formed by winding a wire into a first helix or form; the first helix is then itself wound into a secondary form. The secondary form is one which, once ejected from a delivery catheter, forms a shape having conical section at each opposing end, which conical end diameter decreases to the furthermost points of the device. It generally forms a "submarine" type shape. Desirably, the vaso-occlusive device is of a size and shape suitable for fitting within a vascular cavity (e.g., an aneurysm, perhaps, a fistula). Stiffness of various parts of the coil may be tailored or selected to enhance the ability of the device for its specific applications. Fibrous materials may be woven into the member or tied or wrapped onto it.

The device may be made in a variety of ways. Typically, the member is helically wound in a generally linear fashion to form a first or primary winding. After completion of that step, the primary winding is then wound around an appropriately shaped winding fixture or form and the so-wound assembly is heat treated to help it retain its shape after removal from the winding fixture. Auxiliary fibrous materials are then added by weaving, tying, or other suitable permanent attachment methods.

The device is used simply by temporarily straightening device and introducing it into a suitable catheter, the catheter already having been situated so that its distal opening is within the mouth of the vascular cavity or opening to be filled. The device is then pushed through the catheter and, upon its ejection from the distal end of the catheter into the vascular cavity, assumes its relaxed shape.

The device is typically used in human vasculature to form emboli but may be used in any site in the human body or occlusion such as one produced by the inventive device is desirable.

DESCRIPTION OF THE INVENTION

This invention is a vaso-occlusive device comprising one or more vaso-occlusive helical coils which are formed by winding a wire into a first helix; the first helix is then wound into a secondary form. The secondary form may be held or restrained within a tubular body such as a catheter or introducer into a shape which approximates the shape of the interior of that tubular body. The secondary form is one which, when ejected or pushed from the delivery catheter has a plurality of turns at least one substantially conical portion adjacent to a central cylindrical portion having a diameter approximating the larger end of the conical end. Preferably the device has opposing conical ends separated by a cylindrical coil section.

Figure 1:
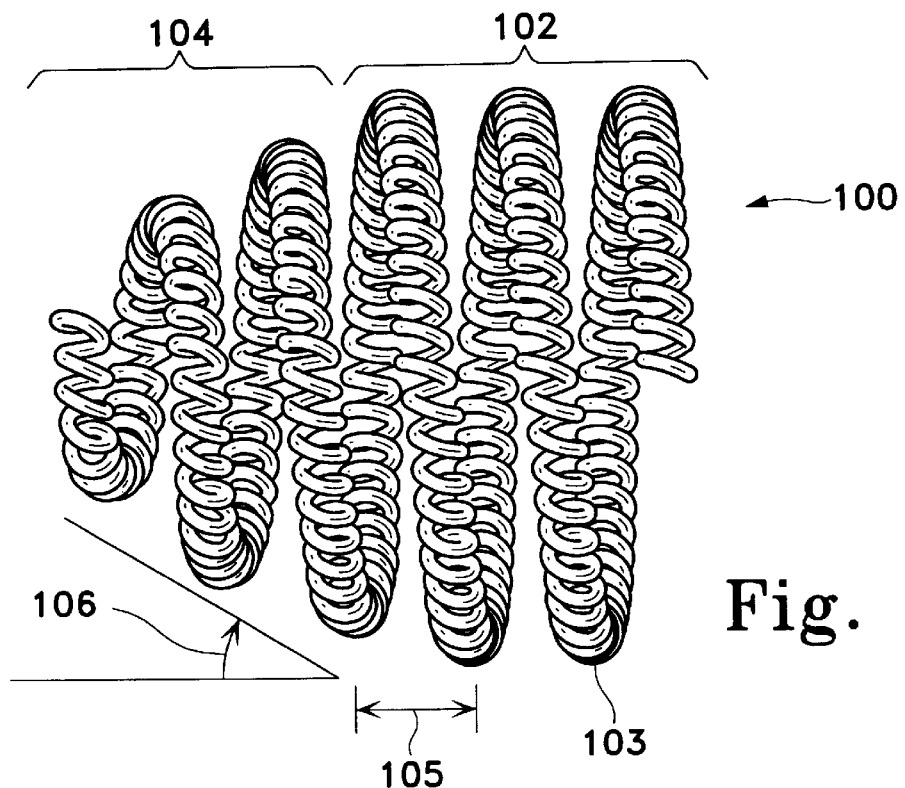
FIG. 1 shows a side view of a variation of the inventive vaso-occlusive device having but a single cone-shaped end and a cylindrical center section.

FIG. 1 shows the most basic variation of (100) of the basic inventive device. In particular, vaso-occlusive device (100), has a generally cylindrical section (102) also known as the mid-section (102) made up of a number of turns (103) helically wound of a primary coil which in turn was helically wound from a wire. The end section (104) has a large end which continues on from the primary winding of central section (102) and creates a taper in section (104) and the taper becomes smaller and smaller as the axis of the coil proceeds. The coil may have a pitch (105) which is fairly loose, that is to say, that the distance between windings in the secondary shape are at least equal to the diameter of the primary coil making up those helical windings. This "looseness" prevents the coil from forming a fixed or pipe-like mass so readily after it has been placed within the human body. This looseness also creates a secondary shape having a fairly large mass in the vasculature which decreases the length of the coil placed within the catheter so to decrease the amount of friction encountered when deploying the coil. A tightly wound coil producing the same deployed coil volume may not be deployable because they simply refuse to be pushed through the catheter using normal pushing techniques. The loose wind discussed here is desirable but not required.

The angle of the coil (106) may be virtually any value between 10° and approaching 90°. Indeed in some variations of the invention which may be considered to be variations having non-conic ends, the end section need only be a spirally wound disk.

The material used in constructing a vaso-occlusive member may be any of a wide variety of materials; preferably, the material chosen is a wire of a radio-opaque material such as a metal or polymer. Suitable metals and alloys for the wire making up the device (100) include the Platinum Group metals, especially platinum, rhodium, palladium, rhenium, and other bio-compatible metals such as tungsten, gold, silver, tantalum, and alloys of these metals. These metals have significant radio-opacity and their alloys may be tailored to accomplish an appropriate blend of flexibility and stiffness. Highly preferred for this service is a platinum/tungsten alloy.

The wire may also be of any of a wide variety of stainless steels if some sacrifice of radio-opacity may be tolerated. Very desirable materials of construction, from a mechanical point of view, are materials which maintain their shape despite being subjected to high stress. Certain "super elastic alloys" include nickel/titanium alloys (48–58 atomic % nickel and optionally containing modest amounts of iron); copper/zinc alloys (38–42% zinc); copper/zinc alloys containing 1–10% by weight of beryllium, silicon, tin, aluminum, or gallium; or nickel/aluminum alloys (36–38 atomic % aluminum). Particularly preferred are the alloys described in U.S. Pat. Nos. 3,174,851; 3,351,463; and 3,753,700. Especially preferred are the super elastic nickel titanium alloys, particularly known as "nitinol". These nickel titanium alloys are very sturdy alloys which will tolerate significant flexing without plastic deformation even when used as a very small diameter wire.

If a super elastic alloy such as nitinol is used in the device, the diameter of the coil wire may be significantly smaller than that used when the relatively more ductile platinum or platinum/tungsten alloy is used as the material of construction.

The coils may be of radiolucent fibers or polymers (or metallic threads or wires coated with radiolucent or radio-opaque polymers) such as Dacron (polyethylene terephthalate or PET), polyglycolic acid, polylactic acid, fluoropolymers such polytetrafluoroethylene, or Nylon (polyamide), or even silk or cotton. Should a polymer be used as a major component of the vaso-occlusive member, it is desirably filled with some amount of a known radio-opaque material such as powdered tantalum, powdered tungsten, bismuth oxide, barium sulfate, and the like.

The coil material is first wound into a primary coil form. The primary coil is typically linear after it has been wound and heat treated. Generally speaking, when the device (100) is formed of a metallic coil and that coil is a platinum alloy or a super elastic alloy such as nitinol, the diameter of the wire used in the production of the coil will be in the range of 0.0005 and 0.006 inches. The wire of such diameter is typically then wound into a primary coil having a primary diameter of between 0.005 and 0.025 inches. For most neurovascular indications, the preferable diameter is between 0.010 and 0.018 inches The axial length of the primary coil will usually fall in the range of 0.5 to 100 cm. more usually 2.4 to 40 cm. Depending on usage, the primary coil may well have 10 to 75 turns per centimeter, preferably 10 to 40 turns per centimeter. All of the dimensions here are provided only as guidelines and are not critical to the invention. However, only dimensions suitable for use in occluding sites within the human body are included in the scope of this invention. The overall diameter of the device as deployed is generally between 3 and 25 millimeters with a range between 3 and 12 millimeters much more common. If this device is used within an aneurysm in the cranial vasculature, these shapes may be treated using devices having those diameters. Of course, such diameters are not a critical aspect of the invention.

Figure 2:
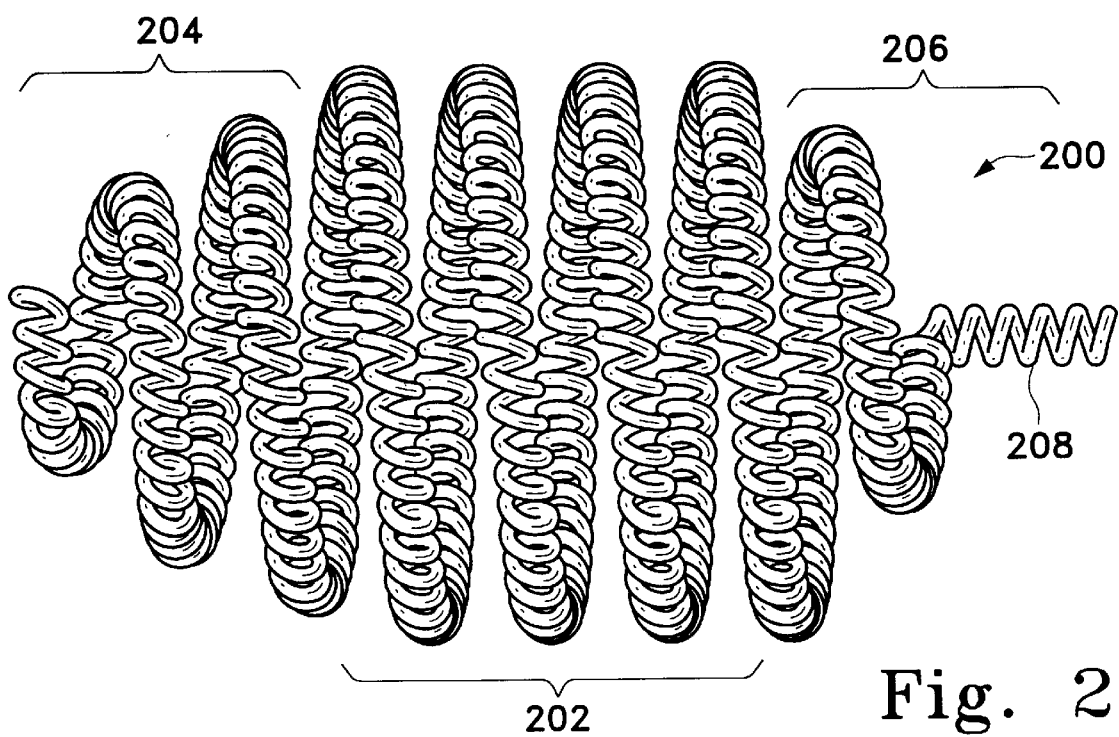
FIG. 2 shows a side view of another variation of the inventive device having conical portions at each end.

FIG. 2 shows another variation of the inventive device (200). In this variation, the center section (202) is two or more times the length of the axial length of the conical end sections (204, 206). The variation (200) also obviously has two opposing ends or sections (204, 206) which are helically wound and have an overall conical shape which is smallest at the opposing extremities of the device. We have found that in some instances, it is desirable to provide a short "tail" such as (208) on the end of the coil which last exits the delivery catheter. This tail (208) prevents the secondary coil turn from hanging in the catheter mouth since the last portion of the device seen by the catheter is straight. The wire in this instance is continuous throughout each of the sections of the device.

Figure 3:
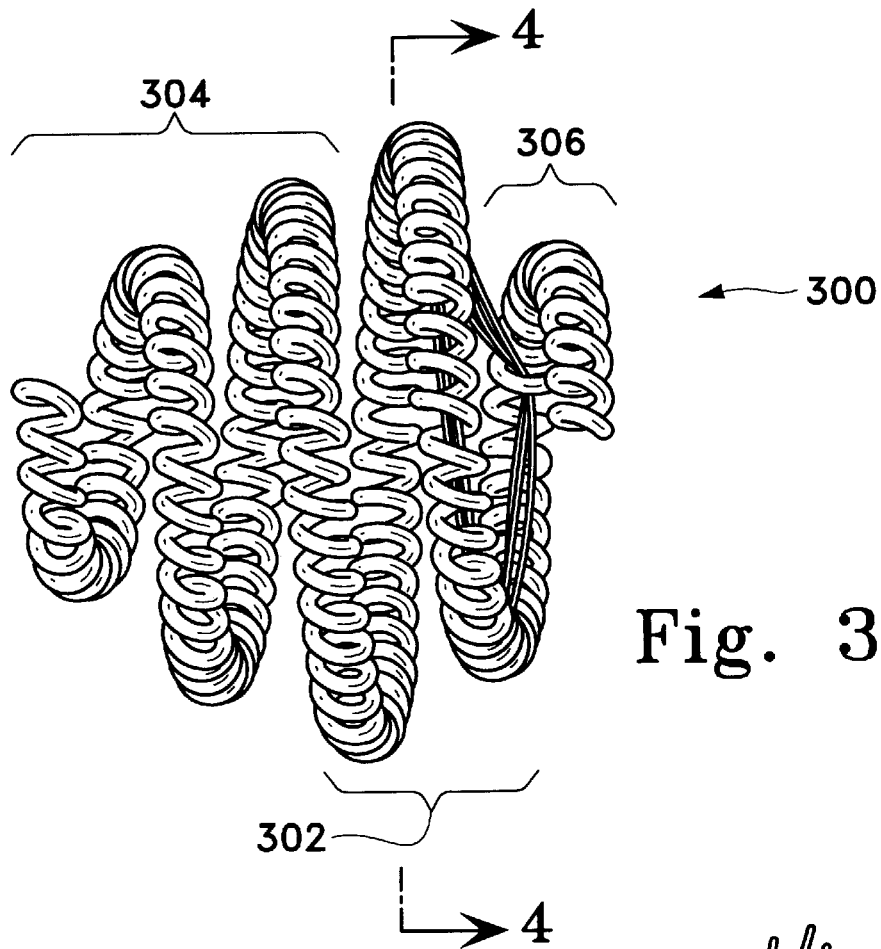
FIG. 3 shows another variation of the inventive device in which the angles of the two conical ends of the device are substantially different.

FIG. 3 shows another variation (300) of the inventive device. In this variation, the central section (302) is quite short in axial length and has but little more than one turn of the coil in the secondary shape within central section (302). Terminal conical section (304) is, perhaps, three times the axial length of center section (302). The opposing end section (306) is also quite short in axial length. The angle of the cone in this variation is found in conical end (306) can approach 90 degrees.

Also contemplated in this invention is the attachment of various fibrous materials to the inventive device for the purpose of adding thrombogenicity to the resulting assembly. A wide variety of fibrous materials have been used in adding to the thrombogenicity of such coils. Including in this group are such well known materials as Dacron (polyethylene terephthalate), polyethylene, polypropylene, silk, Nylon, and cotton.

Figure 4:
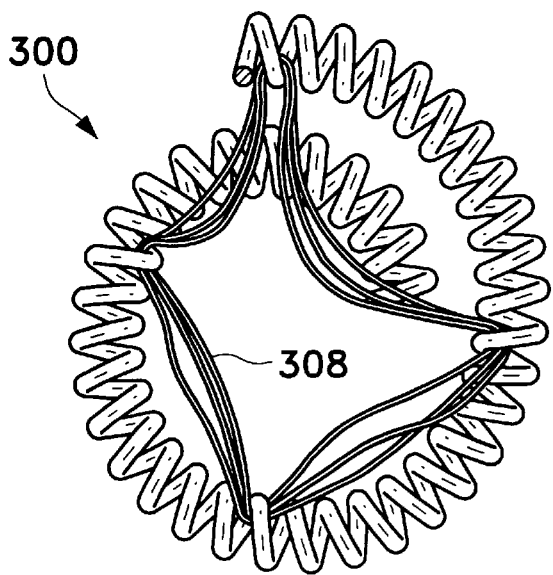
FIG. 4 shows a cross section of the FIG. 3 device showing the interior of fiber placement.

The fibrous materials may be added in a variety of ways, FIG. 4 shows a cross section of the device shown in FIG. 3 and it shows that the fibrous materials (308) found therein are looped around in such a way that they are continuous from end to end and generally may be tied to the end of the coil. Another variation is had by tying the tuft or wrapping the tuft through the turns of the primary coil. Tufts may be tied at multiple sites throughout the coil to provide a vast area of embolus forming sites.

Figure 5:
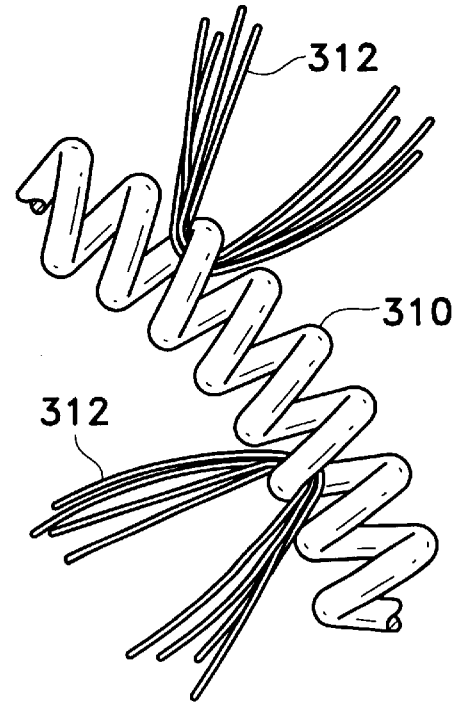
FIG. 5 is a close-up partial side view of a primary coil useful in this invention showing tufted fibers.

FIG. 5 shows a close up of a primary coil (310) having a number of tufts (312) passing through the primary turns of the coil and merely being held in place by turns of the coil itself.

The primary coil may be covered by a fibrous braid such as is shown in U.S. Pat. No. 5,382,259, issued Jan. 17, 1995, to Phelps and Van.

As was noted above, many vaso-occlusive coils are held in place before deployment in a variety of different ways so to provide a c ontrol on the site and time of their deployment. Variations of the invention include the use of electrolytic detachment joints such as is shown in FIG. 6 and mechanical detachment joints such as is shown in FIG. 7.

Figure 6:
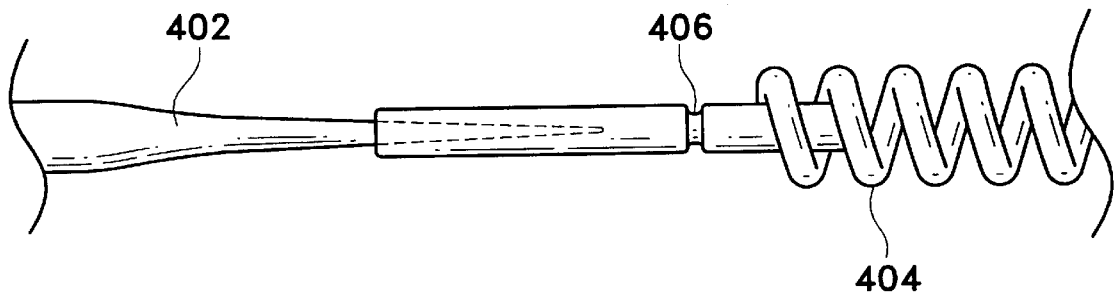
FIG. 6 shows an electrolytically erodible joint useful in deploying this inventive vaso-occlusive device.

Specifically, the electrolytic joint shown in FIG. 6 is described in significant detail in patent such as U.S. Pat. Nos. 5,122,136 and 5,354,295, both to Guglielmi discussed above. In these variations, an insulated pusher (402) is attached to the vaso-occlusive coil (404) via an electrolytically erodible joint (406). A direct current is applied to pusher (402). The current path is, in part, through joint (406) into the ionic medium surrounding the coil upon deployment. Such ionic medium is, in the vasculature, blood or saline solution passing through the deploying catheter. Joint (406) erodes and allows vaso-occlusive device (406) to remain in the body. Vaso-occlusive device (406) may be any of the devices described above with respect to this invention.

Figure 7:
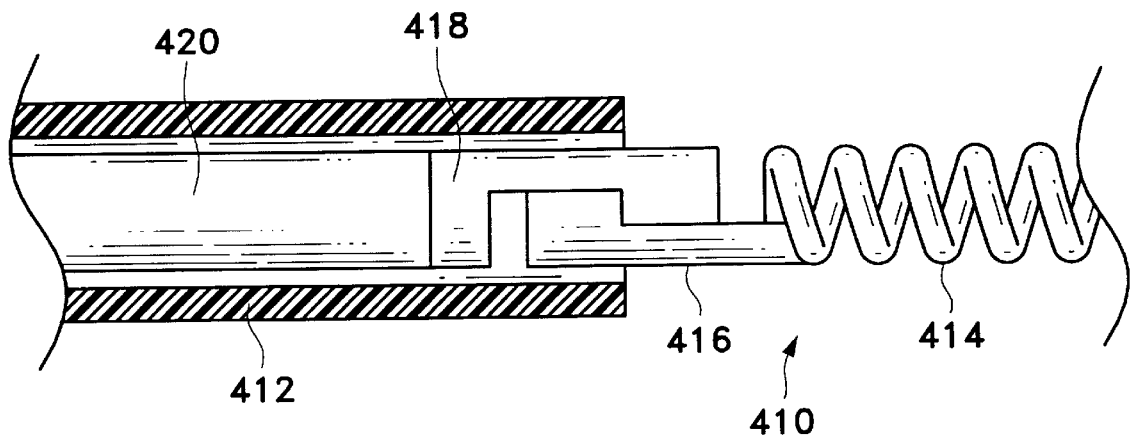
FIG. 7 is a partial cross section side view of a mechanically detachable joint suitable for use with this invention.

Similarly, FIG. 7 shows a mechanically detachable assembly (410) partially housed within a deployment catheter (412). The vaso-occlusive device itself (414) has an end clasp (416) which engages a similar end clasp (418) forming the end of pusher (420). When pusher (420) is forwarded distally so that both clasp (416) and clasp (418) are exterior to catheter (412), the vaso-occlusive device (415) with its attached clasp (416) is free to stay at the chosen site within the human body. Again, vaso-occlusive portion (414) may be any of the devices described above in relation to this invention.

In summary, the manner in which this device is employed or deployed may be found in a variety of other prior publications. In particular, the reader is directed to Ritchart et al., discussed above.

Modification of the above-described variations of carrying out the invention that would be apparent to those of skill in the fields of medical device design generally, and vaso-occlusive devices specifically, are tended to be within the scope of the following claims.

We claim as our invention:

1. A vaso-occlusive device comprising a helically wound primary coil having a diameter wherein said helically wound primary coil further comprises a helically wound secondary structure having a substantially conical portion, said substantially conical portion having a small end and a large end, said large end adjacent a central cylindrical section having a diameter approximating the conical portion large end.

2. The vaso-occlusive device of claim 1 where at least a portion of the helically wound secondary structure has a pitch which is at least twice the diameter of the helically wound primary coil.

3. The vaso-occlusive device of claim 1 further comprising a plurality of fibers fixedly attached to said helically wound primary coil.

4. The vaso-occlusive device of claim 3, wherein the fibers comprise tufts.

5. The vaso-occlusive device of claim 3 wherein the plurality of fibers are looped from turn to turn in said helically wound primary coil.

6. The vaso-occlusive device of claim 1 wherein said helically wound primary coil has at least one detachable end.

7. The vaso-occlusive device of claim 6 wherein the detachable end is electrolytically erodible.

8. The vaso-occlusive device of claim 6 wherein the detachable end is mechanically detachable.

9. The vaso-occlusive device of claim 1 wherein the conical portion further comprises a linear section of the primary coil adjacent the small end of said conical portion.

10. The vaso-occlusive device of claim 1 where said conical portion includes a cone having an angle between about 10° and about 90°.

11. The vaso-occlusive device of claim 10 further comprising a plurality of fibers fixedly attached to said helically wound primary coil.

12. The vaso-occlusive device of claim 1 wherein the primary coil is made of a radio-opaque material.

13. The vaso-occlusive device of claim 12 wherein the radio-opaque material is selected from the group consisting of platinum, rhodium, palladium, rhenium, tungsten, gold, silver, tantalum and alloys of these metals.

14. The vaso-occlusive device of claim 13 wherein the radio-opaque material is a platinum and tungsten alloy.

15. The vaso-occlusive device of claim 12 wherein the radio-opaque material is a super-elastic metal alloy.

16. The vaso-occlusive device of claim 15 wherein the super-elastic alloy is selected from the group consisting of nickel/titanium alloys, copper/zinc alloys, copper/zinc alloys containing beryllium, silicon, tin aluminum or gallium and nickel/aluminum alloys.

17. The vaso-occlusive device of claim 16 wherein the alloy is nitinol.

18. The vaso-occlusive device of claim 12 wherein the radio-opaque material is a polymer.

19. The vaso-occlusive device of claim 18 wherein the polymer is selected from the group consisting of polyethylene terephthalate, polyglycolic acid, polylactic acid, polytetrafluoroethylene, nylon, silk or cotton.

* * * * *